US006583877B2

(12) United States Patent
Norton (10) Patent No.: US 6,583,877 B2
(45) Date of Patent: Jun. 24, 2003

(54) SPECTROSCOPIC MEASUREMENT SYSTEM USING AN OFF-AXIS SPHERICAL MIRROR AND REFRACTIVE ELEMENTS

(76) Inventor: Adam E. Norton, 3696 Ross Rd., Palo Alto, CA (US) 94303

( * ) Notice: Subject to any disclaimer, the term of this patent is extended or adjusted under 35 U.S.C. 154(b) by 0 days.

(21) Appl. No.: 10/150,590

(22) Filed: May 17, 2002

(65) Prior Publication Data

US 2002/0171830 A1 Nov. 21, 2002

Related U.S. Application Data

(63) Continuation of application No. 09/960,024, filed on Sep. 20, 2001, now abandoned, which is a continuation of application No. 09/280,752, filed on Mar. 29, 1999, now Pat. No. 6,323,946, which is a continuation of application No. 09/057,245, filed on Apr. 8, 1998, now Pat. No. 5,917,594.

(51) Int. Cl.[7] .............................. G01J 4/04; G01J 3/447
(52) U.S. Cl. ........................ 356/369; 356/327; 356/636
(58) Field of Search ................................ 356/327, 369, 356/636

(56) References Cited

U.S. PATENT DOCUMENTS

| | | |
|---|---|---|
| 4,039,370 A | 8/1977 | Kleinknecht |
| 4,141,780 A | 2/1979 | Kleinknecht et al. |
| 4,200,396 A | 4/1980 | Kleinknecht et al. |
| 4,303,341 A | 12/1981 | Kleinknecht et al. |
| 4,330,213 A | 5/1982 | Kleinknecht et al. |
| 4,408,884 A | 10/1983 | Kleinknecht et al. |
| 4,710,642 A | 12/1987 | McNeil |
| 4,790,659 A | 12/1988 | Erman et al. |
| 4,905,170 A | 2/1990 | Forouhi et al. |
| 5,164,790 A | 11/1992 | McNeil et al. |
| 5,241,369 A | 8/1993 | McNeil et al. |
| 5,329,357 A | 7/1994 | Bernoux et al. |
| 5,381,233 A | 1/1995 | Chao et al. |
| 5,416,594 A | 5/1995 | Gross et al. |
| 5,432,607 A * | 7/1995 | Taubenblatt ................ 356/364 |
| 5,607,800 A | 3/1997 | Ziger |
| 5,608,526 A | 3/1997 | Piwonka-Corle et al. |
| 5,739,909 A * | 4/1998 | Blayo et al. ................ 356/369 |
| 5,757,671 A | 5/1998 | Drevillon et al. |
| 5,835,221 A | 11/1998 | Lee et al. |
| 5,867,276 A | 2/1999 | McNeil et al. |
| 5,923,423 A | 7/1999 | Sawatari et al. |
| 5,956,148 A | 9/1999 | Celii |
| 5,963,329 A | 10/1999 | Conrad et al. |
| 6,031,615 A | 2/2000 | Meeks et al. |
| 6,118,525 A | 9/2000 | Fossey et al. |
| 6,323,946 B1 | 11/2001 | Norton |
| 6,483,580 B1 | 11/2002 | Xu et al. |

OTHER PUBLICATIONS

"Optical dispersion relations for amorphous semiconductors and amorphous dielectrics," A.R. Forouhi et al., *Physical Review B*, vol. 34, No. 10, Nov. 15, 1986, pp. 7018–7026.
"Optical properties of crystalline semiconductors and dielectrics," A.R. Forouhi et al., *Physical Review B*, vol. 38, No. 3, Jul. 15, 1988, pp. 1865–1873.

(List continued on next page.)

*Primary Examiner*—F. L. Evans (57) ABSTRACT

Achromatic optics may be employed in spectroscopic measurement systems. The achromatic optics comprises a spherical mirror receiving a beam of radiation in a direction away from its axis and a pair of lenses: a positive lens and a negative meniscus lens. The negative meniscus lens corrects for the spherical aberration caused by off-axis reflection from the spherical mirror. The positive lens compensates for the achromatic aberration introduced by the negative lens so that the optics, as a whole, is achromatic over visible and ultraviolet wavelengths. Preferably, the two lenses combined have zero power or close to zero power. By employing a spherical mirror, it is unnecessary to employ ellipsoidal or paraboloidal mirrors with artifacts of diamond turning which limit the size of the spot of the sample that can be measured in ellipsometry, reflectometry or scatterometry.

32 Claims, 3 Drawing Sheets

OTHER PUBLICATIONS

"Optical characterization of amorphous and polycrystalline silicon films," E. Ibok et al., *Solid State Technology*, Aug. 1995.

"Convergence of the coupled–wave method for metallic lamellar diffraction gratings," L. Li et al., *Journal of the Optical Society of America A*, vol. 10, No. 6, Jun. 1993, pp. 1984–1188.

"Multilayer modal for diffraction gratings of arbitrary profile, depth, and permittivity," L. Li, *Journal of the Optical Society of America A*, vol. 10, No. 12, Dec. 1993, pp. 2581–2591.

"A modal analysis of lamellar diffraction gratings in conical mountings," L. Li, *Journal of Modern Optics*, vol. 40, No. 4, 1993, pp. 553–573.

"Metrology of subwavelength photoresist gratings using optical scatterometry," C.J. Raymond et al., *J. Vac. Sci. Technol. B*, vol. 13, No. 4, Jul./Aug. 1995, pp. 1484–1495.

"Line size effects on ultraviolet reflective spectra," D.H. Ziger et al., *Opt. Eng.*, vol. 36, No. 1, Jan. 1997, pp. 243–250.

Scatterometry and the Simulation of the Diffraction–Based Metrology, S. Sohail et al., *Microlithography World*, Jul./Aug./Sep. 1993, pp. 5–16.

"A broadband UV small spot spectroscopic ellipsometer," T.R. Corle, *SPIE Microlithography*, 1995, pp. 1–12.

"Rigorous coupled–wave analysis of planar–grating diffraction," M.G. Moharam et al., *J. Opt. Soc. Am.*, vol. 71, No. 7, Jul. 1981, pp. 811–818.

"Stable implementation of the rigorous coupled–wave analysis for surface–relief gratings: enhanced transmittance matrix approach," M.G. Moharam et al., *J. Opt. Soc. Am. A.*, vol. 12, No. 5, May 1995, pp. 1077–1086.

"Analysis and Applications of Optical Diffraction by Gratings," T.K. Gaylord et al., *Proceedings of the IEEE*, vol. 73, No. 5, May 1985, pp. 894–937.

"Ultraviolet–visible ellipsometry for process control during the etching of submicrometer features," N. Blayo et al., *J. Opt. Soc. Am. A*, vol. 12, No. 3, Mar. 1995, pp. 591–599.

* cited by examiner

SPECTROSCOPIC MEASUREMENT SYSTEM USING AN OFF-AXIS SPHERICAL MIRROR AND REFRACTIVE ELEMENTS

CROSS REFERENCE TO RELATED APPLICATIONS

This application is a continuation of U.S. patent application Ser. No. 09/960,024, filed Sep. 20, 2001 (now abandoned), which is a continuation of U.S. patent application Ser. No. 09/280,752, filed Mar. 29, 1999, now U.S. Pat. No. 6,323,946, which is a continuation of U.S. patent application Ser. No. 09/057,245, filed Apr. 8, 1998, now U.S. Pat. No. 5,917,594.

BACKGROUND OF THE INVENTION

This invention relates in general to optical measurement instruments, and in particular, to an optical spectroscopic measurement system including a spherical mirror that focuses radiation in an off-axis configuration and refractive elements.

Ellipsometers are used to measure thickness and optical constants of thin films as well as the optical constants of bulk materials. They function by directing a beam of light on the sample at a high angle of incidence and analyzing the effect of the sample on the polarization of the reflected or transmitted beam. Ellipsometers used to measure patterned samples, such as integrated circuits, must be able to measure within small features (often 50 microns wide or less) surrounded by a completely different material or film stack. Even an extremely small amount of light falling on the surrounding features and collected by the detector can cause errors in the measurements. Thus the optical systems focusing light onto the sample and collecting light from the sample must be designed to minimize the radiation falling on or detected from areas outside the smallest measurable feature, and this condition must be achieved over the entire range of wavelengths used by the instrument. It is also necessary for the optical system to have a minimal effect on the polarization of the light. In addition the optics must not physically interfere with the flat sample which is often very large.

If the wavelength range is relatively narrow, refractive microscope objectives work adequately to focus a small spot onto the sample. When the wavelength range is large, refractive objectives exhibit too much chromatic aberration. Reflecting objectives (such as the Schwarzchild design) using a concave and convex mirror are well known and have zero chromatic aberration. However if any significant demagnification is required to produce a small spot and high numerical aperture (NA), then the angles of incidence on the internal mirrors are too high and the polarization is altered. De-magnification is required because the light must first pass through a polarizing prism which can only handle a small numerical aperture beam. This must then be converted to a larger NA beam by the focusing optics to produce a small spot.

Theoretically, the ideal reflective optical element to focus a collimated beam (such as from a laser light source) onto the sample would be an off-axis paraboloidal mirror, and the ideal shape to focus a small source (such as a fiber optic end) onto the sample would be an off-axis ellipsoidal mirror. An off-axis ellipsoidal mirror has been used before in a spectroscopic ellipsometer, such as in U.S. Pat. No. 5,608,526. Such an aspheric mirror can provide a wide range of possible demagnifications with a small angle of incidence on its surface. It has no chromatic aberration and (theoretically at least) has no other aberration. These mirrors can also be combined with some types of low or zero power refractive elements with minimal impact on the optical performance. Examples of such elements are compensators or waveplates (frequently used in ellipsometry to deliberately change the polarization state), windows (used to control air currents or to enclose the sample in a vacuum or gas), apodizing filters (such as ones described in U.S. patent application Ser. No. 08/835,533, filed on Apr. 8, 1997), other optical filters (useful for calibration and diagnostics) or low power lenses (potentially useful for adjusting focus or magnification). Generally, the maximum tolerable thickness or power of these elements is inversely dependent on the NA of the beam.

The main problem with these aspheric mirrors is that they are made by a single-point diamond turning process that leaves a surface with a figure error composed of a multitude of grooves and ridges covering a broad range of spatial frequencies. Each spatial frequency component diffracts light at a characteristic angle increasing the stray light outside the desired small spot on the sample. This characteristic error produced by diamond turning is one of the main factors limiting the minimum box size within which accurate ellipsometric measurements can be made. Aspheric mirrors made with conventional polishing would perform better, but are very expensive given the aperture and focal lengths needed by this system. Techniques also exist for replicating aspheric mirrors in a thin layer of epoxy on glass, but the performance and durability of these mirrors has not yet been proven in this application.

To eliminate the diamond turning grooves, it would therefore be desirable to replace the aspheric mirror with an optical system composed of only conventionally polished spherical surfaces. The optical system still must meet all the requirements discussed above. If the aspheric mirror is replaced with a tilted spherical mirror, the spherical aberration, astigmatism and coma would be much too great. There are many designs that exist to correct the aberrations from a tilted spherical mirror. But none can be adapted to work adequately for ellipsometry.

U.S. Pat. Nos. 4,208,585, 4,196,961, and 3,598,468 use a tilted glass plate either before or after the tilted spherical mirror. This approach suffers from many drawbacks when applied to ellipsometry systems. Among these are space constraints, inadequate aberration correction, and excessive chromatic aberration when used in the ultraviolet (UV) and visible wavelengths.

U.S. Pat. Nos. 4,230,394 and 4,588,269 use the approach of having two spherical mirrors tilted in orthogonal planes. This design does not correct the aberrations adequately for ellipsometry purposes especially considering the approximate 18:1 demagnification required for many ellipsometry systems.

U.S. Pat. No. 4,226,501 uses a relay system composed of 4 spherical mirrors to correct the aberrations from a tilted mirror. While the incident angle on each mirror is relatively small, the combined effect of four mirrors would have too large of an effect on the polarization of the light.

U.S. Pat. No. 5,168,386 uses a single positive meniscus lens before or after the tilted spherical mirror, or the lens can be placed where both incident and reflected rays are intercepted by it. This design works well for narrow wavelength ranges, but has too much chromatic aberration for a wide wavelength range, such as one including visible and ultraviolet (UV) wavelengths.

U.S. Pat. No. 4,135,820 uses a faceted beam combiner. The corners of the facets would scatter too much light into adjacent patterns for ellipsometry purposes, and the angle of incidence on the facets is too large.

A tilted spherical mirror can also be thought of as an off-axis section of a much larger axially symmetric spherical mirror (the axis defined by the object and image points). For conjugate ratios other than 1:1, the axially symmetric spherical mirror will exhibit pure spherical aberration. An off-axis segment will produce aberration that seems to include components of astigmatism and coma, and a tilted spherical mirror is often referred to as-having such aberrations. However, for the purposes of lens design, it is more useful to consider the aberration of an off-axis segment as being a subset of the spherical aberration of the larger, axially symmetric mirror.

A design that corrects well over the entire aperture of a low F# system could be adapted for use in ellipsometry by cutting out off-axis segments of all the mirrors and lenses. There are many such catadioptric designs that use lenses to correct a spherical mirror. Classic examples include the Schmidt camera and Maksutov telescope (see Kingslake, "Lens Design Fundamentals" chap. 14, Academic Press, Inc., San Diego, Calif., 1978). The chief problem with adapting most of these designs is that they have too much chromatic aberration when used from the deep UV through near infrared (IR). The classic way to correct for chromatic aberration in lens is to make it using 2 elements made of glasses having different dispersions. Chromatic aberration in the UV is a particular problem because there are only a limited number of materials that transmit UV, and only two that transmit deep UV that are also not birefringent. Birefringent materials alter the polarization of the beam and are therefore not desirable unless used advantageously in polarizers or waveplates. Furthermore, the design goals of most of these systems differ from that of ellipsometry in that most optical systems must produce a well-corrected image over a fairly large field whereas in many ellipsometry systems the system needs to be optimized only at substantially a single point in the center of the field.

There is also a class of catadioptric systems known as ring-field systems that are well corrected and have little chromatic aberration over a large wavelength range. Such systems are exemplified by U.S. Pat. No. 3,748,015. The main problem with such lens systems for ellipsometry application is that the demagnification is limited to less than about 5:1. These systems also tend to have high angles of incidence on the mirrors which is undesirable. Furthermore, they are designed to have good imaging characteristics over a large, ring-shaped field which makes them unnecessarily complicated for ellipsometry purposes.

None of the existing systems is entirely satisfactory for use in ellipsometry or other spectroscopic measurement systems. It is therefore desirable to propose broadband spectroscopic measurement systems using a spherical mirror with improved characteristics.

SUMMARY OF THE INVENTION

A first aspect of the invention is directed towards an apparatus for performing spectroscopic ellipsometry measurements on a sample, comprising a source which emits broadband radiation, a polarizer that polarizes the broadband radiation, to produce a sampling beam, and substantially achromatic optics that focuses the sampling beam to a small spot on the sample, said optics including a spherical mirror and at least two refractive elements, said sampling beam incident on the mirror from a direction away from the axis of the mirror, wherein at least one of said elements corrects spherical aberration caused by off-axis reflection from the mirror. The apparatus further comprises an analyzer that analyzes radiation of the sampling beam that has interacted with the sample, thereby producing an output beam, detector means for detecting the outputs to provide a detected output and means for processing the detected output to determine changes of polarization state in amplitude and phase of the sampling beam caused by interaction with the sample. In the context of this aspect as well as other aspects of the invention, a polarizer and an analyzer can include any element, or a combination of elements, that modifies the polarization of radiation and the axis of the mirror may be defined with respect to its center of curvature and center of the illuminated area on the mirror.

Another aspect of the invention is directed towards an apparatus for performing spectroscopic measurements on a sample, comprising a source which provides a sampling beam of broadband radiation for interaction with a sample; detector means; and optics that focuses the sampling beam to small spot on the sample or that focuses, from a small spot on the sample into a modified beam to the detector means, radiation of the sampling beam that has interacted with the sample. Said optics includes a spherical mirror and at least two lenses, said sampling or modified beam incident on the mirror from a direction away from an axis of the mirror. At least one of the lenses corrects spherical aberration caused by off-axis reflection from the mirror, said optics being substantially achromatic over visible and ultraviolet wavelengths.

Yet another aspect of the invention is directed towards an apparatus for performing spectroscopic measurements on a sample, comprising a source which provides a sampling beam of broadband radiation for interaction with the sample; detector means; and substantially achromatic optics that focuses the sampling beam to a small spot on the sample or that focuses, from a small spot on the sample onto a modified beam to the detector means, radiation of the sampling beam that has interacted with the sample. The optics includes a spherical mirror and at least two lenses. The sampling or modified beam is incident upon the mirror from a direction away from an axis of the mirror. At least one of the lenses is a meniscus lens that corrects spherical aberration caused by off-axis reflection from the mirror.

One more aspect of the invention is directed towards an apparatus for performing spectroscopic measurements on a sample, comprising a source which provides a sampling beam of broadband radiation for interaction with a sample; detector means; and substantially achromatic optics that focuses the sampling beam to a small spot on the sample or that focuses, from a small spot on the sample into a modified beam to the detector means, radiation of the sampling beam that has interacted with the sample. The optics includes a spherical mirror and at least two lenses. Said sampling or modified beam is incident on the mirror from a direction away from the axis of the mirror. At least one of the lenses corrects spherical aberration caused by off-axis reflection from the mirror, wherein two of said lenses have substantially opposite magnification powers.

One more aspect of the invention is directed towards a method for performing spectroscopic ellipsometry measurements on a sample, comprising providing broadband radiation; polarizing the broadband radiation to produce a sampling beam; and focusing the sampling beam to a small spot on the sample by means of substantially achromatic optics that includes a spherical mirror and at least two refractive elements. The sampling beam is incident on the mirror from a direction away from an axis of the mirror, wherein at least one of the elements corrects spherical aberration caused by off-axis reflection from the mirror. The method further comprises analyzing radiation of the sampling beam that has interacted with the sample, thereby producing an output beam; detecting the output beam to provide a detected output; and processing the detected output to determine changes of polarization state in amplitude and phase of the sampling beam caused by interaction with the sample.

Yet another aspect of the invention is directed towards a method for performing spectroscopic measurements on a sample, comprising providing a sampling beam of broadband radiation for interaction with a sample; and focusing the sampling beam to a small spot on the sample, or radiation of the sampling beam that has interacted with the sample from a small spot of the sample into a modified beam, by means of optics, said optics including a spherical mirror and at least two lenses. The sampling or modified beam is incident on the mirror from a direction away from an axis of the mirror, wherein at least one of the lenses corrects spherical aberration caused by off-axis reflection from the mirror, the optics being substantially achromatic over visible and ultraviolet wavelengths. The method further comprises detecting radiation of the sampling beam that has interacted with the sample.

One more aspect of the invention is directed towards an apparatus for performing spectroscopic ellipsometry measurements on a sample, comprising a source which emits broadband radiation; a polarizer that polarizes the broadband radiation, to produce a sampling beam for interaction with the sample; an analyzer; and substantially achromatic optics that focuses, from a small spot on the sample into a modified beam to the analyzer, radiation of the sampling beam that has interacted with the sample, said analyzer providing an output beam in response thereto. The optics includes a spherical mirror and at least two refractive elements. The modified beam is incident on the mirror from a direction away from an axis of the mirror. At least one of the elements corrects spherical aberration caused by off-axis reflection from the mirror. The apparatus further comprises detector means detecting the output beam to provide the detected output; and means for processing the detected output to determine changes of polarization state in amplitude and phase of the sampling beam caused by interaction with the sample.

Yet one more aspect of the invention is directed for a method for performing spectroscopic ellipsometry measurements on a sample, comprising providing broadband radiation; polarizing the broadband radiation to produce a sampling beam for interaction with a sample; and focusing by means of optics, from a small spot on the sample into a modified beam, radiation of the sampling beam that has interacted with the sample. The optics includes a spherical mirror and at least two refractive elements, said modified beam being incident on the mirror from a direction away from a axis of the mirror, wherein at least one of said elements corrects spherical aberration caused by off-axis reflection from the mirror. The method further comprises analyzing radiation of the modified beam to produce an output beam; detecting the output beam to provide a detected output; and processing the detected output to determine changes of polarization state in amplitude and phase of the sampling beam caused by interaction with the sample.

BRIEF DESCRIPTION OF THE DRAWINGS

For simplicity in description, identical parts in the different figures are identified by the same numerals.

DETAILED DESCRIPTION OF THE PREFERRED EMBODIMENT

Figure 1:
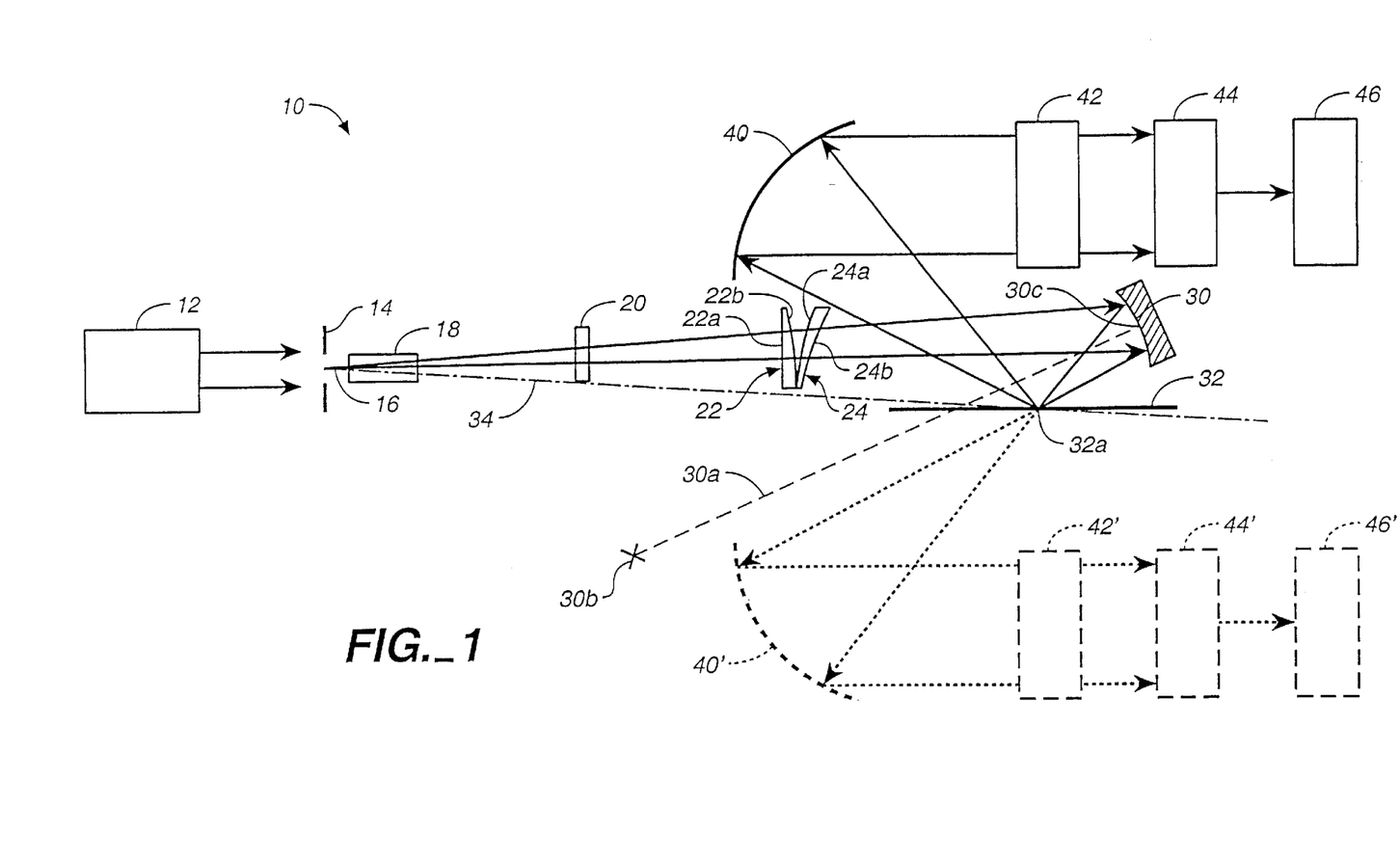
FIG. 1 is a schematic view of an ellipsometer employing a spherical mirror and a refractive system to illustrate a first embodiment of the invention.

In reference to system 10 of FIG. 1, a broadband radiation source (preferably a xenon arc lamp) 12 supplies radiation through an aperture 14 along an optical path 16 to a polarizer 18. Polarizer 18 polarizes the radiation and the polarized radiation is passed through an apodizer 20 which also acts as an aperture stop for the system 10. The beam from apodizer 20 is passed through lens 22 and 24 to a spherical mirror 30 which focuses the radiation onto a small spot 32a on the surface of sample 32. An image of the aperture is thus focused onto an image plane at the spot 32a, and the dotted line 34 connecting the aperture and the spot is the optical axis of system 10. The radiation reflected from sample 32 is collected by a collection mirror 40 which focus the collected light to an analyzer 42 and a spectrometer 44 with its associated aperture (not shown). The output of the spectrometer is analyzed by a computer 46 to determine the change in amplitude and phase of polarization caused by interaction of the sampling beam with the sample.

By replacing an ellipsoidal mirror of U.S. Pat. No. 5,608, 526 with a spherical mirror as in FIG. 1, the limiting factor of errors produced by diamond turning is eliminated and the minimum box size within which accurate ellipsometric measurements can be made is no longer so limited. The box size achieved in this invention can be 40 by 40 microns or smaller. In the preferred or other embodiments, a polarizer and an analyzer can include any element that modifies the polarization of radiation, such as a linear polarizer and a wave plate or an acousto-optic modulator. The axis 30a of the mirror may be defined with respect to its center of curvature 30b and center 30c of the illuminated area on the mirror in the preferred embodiment as shown in FIG. 1. The axis of mirrors may be defined in a similar manner for the configurations in FIGS. 2 and 3.

Instead of collecting and detecting radiation that is reflected by a sample 32, where the sample transmits radiation, it is also possible to detect radiation that is transmitted through the sample, such as by means of mirror 40', which focuses the collected radiation to analyzer 42' and spectrometer 44' and computer 46', shown in dotted lines in FIG. 1, and to thereby determine the change in amplitude and phase of polarization caused by interaction of the sampling beam with the sample. In still other variations, it may be possible to collect radiation that is scattered by or through the sample to determine the change in amplitude and phase of polarization caused by interaction of the sampling beam with the sample.

Refractive element 22, in the preferred embodiment, is a positive lens and refractive element 24 is preferably a negative meniscus lens. In the preferred embodiment, elements 22, 24 are made from the same optical material that is not birefringent in the ultraviolet wavelength range, as well as in other wavelength ranges, such as the visible.

Suitable optical materials for elements 22, 24 include calcium fluoride and fused silica.

As shown in FIG. 1, the beam of radiation 46 incident on mirror 30 is at an angle to the axis 30a of the mirror, a condition where the mirror reflects beam 46 in an off axis position. Because of the off axis position of the mirror relative to the beam 46, off axis reflection of the mirror would normally cause spherical aberration. The negative meniscus lens is used to correct the spherical aberration caused by such off axis reflection from mirror 30.

To compensate for the chromatic aberration introduced by lens 24, a positive lens 22 is employed, so that when considered as a whole, lenses 22, 24 and the spherical mirror 30 form a substantially achromatic optical device over the visible and ultraviolet wavelengths.

Given all of the above, one of the goals of the present invention was to design a replacement optics for the ellipsoidal off axis mirror for use in a small-spot spectroscopic ellipsometer that preferably has the following characteristics: it is made from elements with all spherical surfaces. It is achromatic between preferably at least 250 to 800 nanometers and more preferably between 190 to 850 nanometers. The aberrations may need to be corrected for close to diffraction limited performance in the center of the field only. As indicated above, the optics comprises an off axis spherical mirror and at least two lenses.

Where the size of the spot in the image plane is determined by the illumination optics, the chief ray preferably has an angle of incidence on the sample that could range from between about 60 and 80 degrees depending on the ellipsometer system design. Where the size of the spot in the image plane is determined by the collection optics, the chief ray preferably has an angle of collection from the sample that could range from between 60 and 80 degrees, also depending on the ellipsometer system design.

The conjugate ratio preferably varies between 1:1 and infinity:1 depending on the requirements of the ellipsometer design. The optics using spherical mirror preferably does not have a large effect on the polarization of the light beam or otherwise interfere with the large, flat sample. The optics preferably is compatible with thin, zero or low power refractive elements inserted into the long conjugate side as was the case with the original aspheric mirror system.

Element 20 is preferably an apodizing filter on a fused silica substrate. Refractive element 22 is a positive lens made preferably from calcium fluoride. Element 24 is a negative meniscus lens made from the same material. Preferably, elements 22, 24 have substantially the same Abbe numbers. The apodizer acts as the aperture stop for the system. Lenses 22, 24 have their vertices located on the axis 34 defined by the aperture 14 and the image on the sample. Optionally, lenses 22, 24 may be translated and tilted together slightly to marginally extend the wavelength range of the chromatic correction. The sample 32 is tilted 90 degrees from the usual image plane so that there can be a high angle of incidence on the sample with a low angle of incidence on the mirror. This also allows the object and optics to all lie on the same side of the sample. The rest of the prescription is given below, where surfaces 22a, 24a of lenses 22, 24 face the incoming beam from source 12, and surfaces 22b, 24b of the lenses face away from the incoming beam:

| Surface | Radius of curvature [mm] | Thickness to next surface [mm] | Tilt [degrees] |
| --- | --- | --- | --- |
| Object | 0 | 261.117 | 0 |
| Apodizer | 0 | 2.0 | 0 |
| Apodizer back | 0 | 3.0 | 0 |
| surface 22a | 116.426 | 2.0 | 0 |
| surface 22b | −38.884 | 0 | 0 |
| surface 24a | 28.253 | 0.5 | 0 |
| surface 24b | 14.145 | 61.382 | 0 |
| Mirror | 36.267 | −19.241 | 0 |
| Sample | 0 | | 90 |

All distances are measured along the axis joining the object and image. The apodizer aperture half diameter is 3 mm and it is decentered 4.5 mm above the axis. The angle of incidence of the chief ray on the sample is 72.95 degrees, and the demagnification is 16.98.

The numerical aperture and angle of incidence can be changed by varying the size and position of the apodizer. The axial position of the apodizer is not too important as long as it is not so close to the object plane that it creates vignetting or a highly non-telecentric condition on the sample side. Putting it farther from the object also allows it to be larger and easier to manufacture.

If this system were designed for a narrow wavelength range, then element 24 alone, with different curvatures, would be adequate to correct the spherical aberration introduced by the tilted spherical-mirror. To correct the chromatic aberration, element 22 is added. Element 22 adds only a small amount of its own spherical aberration which is also corrected by element 3. However element 22 is shaped to create the opposite balancing chromatic aberration to element 24. In other words, lens 24 corrects (preferably over corrects) the spherical aberration caused by the off axis reflection by mirror 30. Lens 24 also introduces chromatic aberration of its own. Lens 22 not only compensates for the chromatic aberration caused by lens 24, but also compensates for any spherical aberration caused by lens 24. While ideally the combination of lenses 22, 24 has zero power, in some systems, the combination of the two lenses having some power may not significantly affect system performance.

The design process is one where the curvatures are optimized to balance chromatic versus spherical aberration. One factor in the designer's favor is that the optimization only has to be achieved in the center of the field. Another positive factor is that the aberrations do not have to be corrected over the missing on-axis portion of the aperture. The surfaces of elements 22, 24 facing each other have different shapes or curvatures.

Calcium fluoride is used for the lenses 22, 24 because it transmits well in the UV and has low dispersion minimizing the chromatic aberration that must be corrected. In practice, calcium fluoride may have too much residual, stress-induced birefringence. In this case, fused silica could be used with only marginally worse results. Tilting the lens group helps the fused silica design more than the calcium fluoride design. If the wavelength range is narrowed to use wavelengths above 300 nm, a few more glass types become transparent, and above 350 nm many other glass types become transparent. For the reduced wavelength range, a less expensive glass may be used, and perhaps a marginal improvement in performance by selecting two glasses with different dispersion. The UV materials produce excellent results over the reduced wavelength range.

In practice, the design is optimized for a given configuration using ray tracing software such as Zemax (available from Focus Software Inc. of Tucson, Ariz. There may be many combinations of variables and constraints that could be used to optimize this design. In one experiment, the two conjugate distances and the aperture position and size are fixed. Thicknesses of the two lenses were also fixed to be as thin as practical with the centers touching. All 6 curvatures are allowed to vary as well as the position of the refractive lens group. The merit function minimized RMS wavefront error over a wavelength range of 210 to 800 nanometers. The resulting peak-to-valley wavefront error was less than 0.15 waves for all wavelengths. The wavelength range can be extended to 190 to 850 nm. with only a slight degradation in performance.

A remaining issue with this design is that the effect on polarization due to the angle of incidence on the optical surfaces is not negligible even though the contribution from the two refractive lenses is less than that from the mirror. Such effects may be calculated and then subtracted to reduce their effects.

There are several possible variations of this design. The chief one is that the design can be optimized for a wide range of magnifications and angles of incidence on the wafer. Various planar optical elements mentioned previously can be inserted in the long conjugate of the disclosed version of the design if the thickness is less than about 20 mm. If the lenses are redesigned to compensate, then the planar elements can be even thicker. An aplanatic element having its surfaces perpendicular to the ray fan can be inserted with almost any thickness either before or after the mirror. A lens with low power can be inserted almost anywhere in the path as long as the rest of the elements are re-optimized to accommodate it. Each existing lens can also be "split" into two or more lenses to give more degrees of freedom in the optimization. Instead of tilting the lens pair for marginal performance improvement, the two elements can be translated relative to each other. The spherical mirror can also be made a mangin mirror for a slight performance improvement.

Instead of lenses, the two refractive elements 22, 24 may also be prisms or other optical elements having the required functions as described above.

Figure 2:
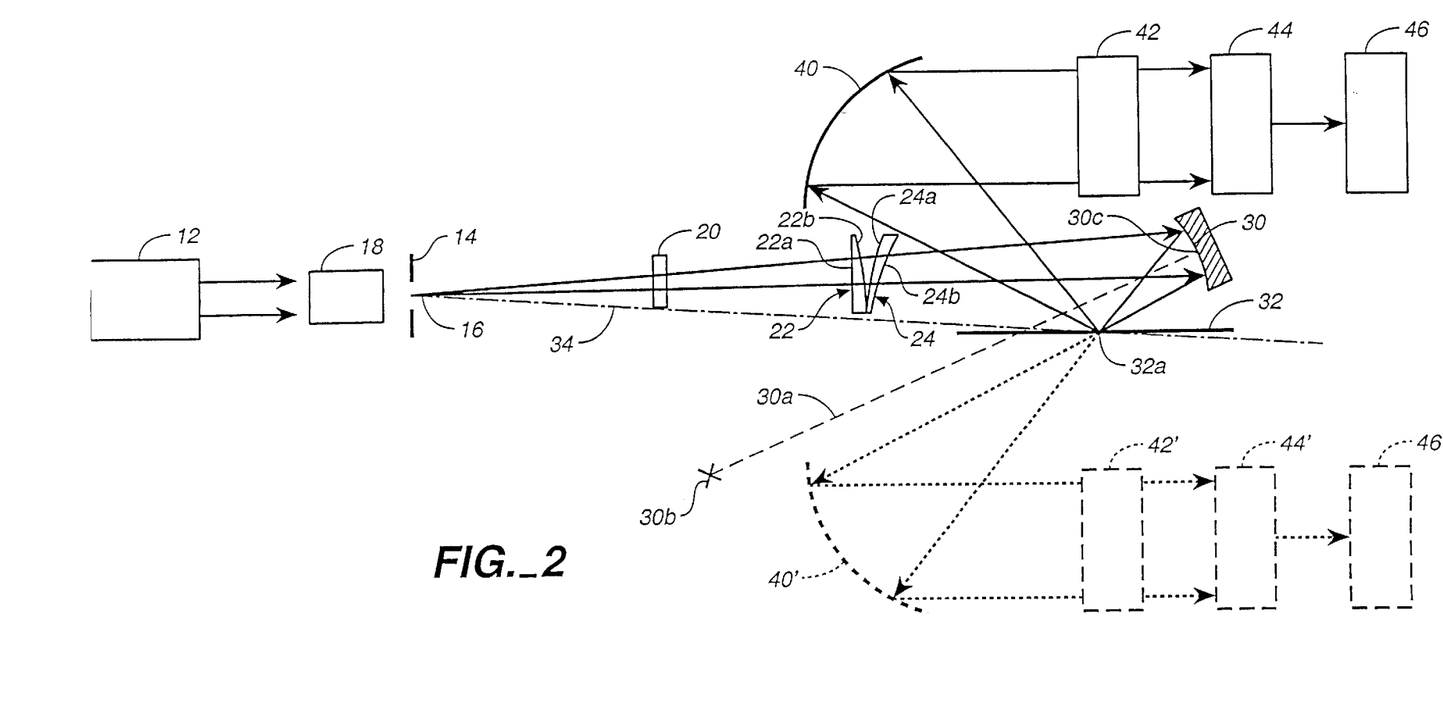
FIG. 2 is a schematic view of an ellipsometer similar in construction to the ellipsometer of FIG. 1, but where an input aperture is placed at a different location in an optical path of the ellipsometer to illustrate a second embodiment of the invention.

FIG. 2 is a schematic view of an ellipsometer similar in construction to the ellipsometer of FIG. 1, but where an input aperture is placed at a different location in an optical path of the ellipsometer to illustrate a second embodiment of the invention. As shown in FIG. 2, aperture 14 may be placed between the polarizer 18 and the apodizer 20, instead of between the source 12 and the polarizer 18 as in FIG. 1. Computer 46, 46' have been omitted in FIG. 2 to simplify the drawing.

Figure 3:
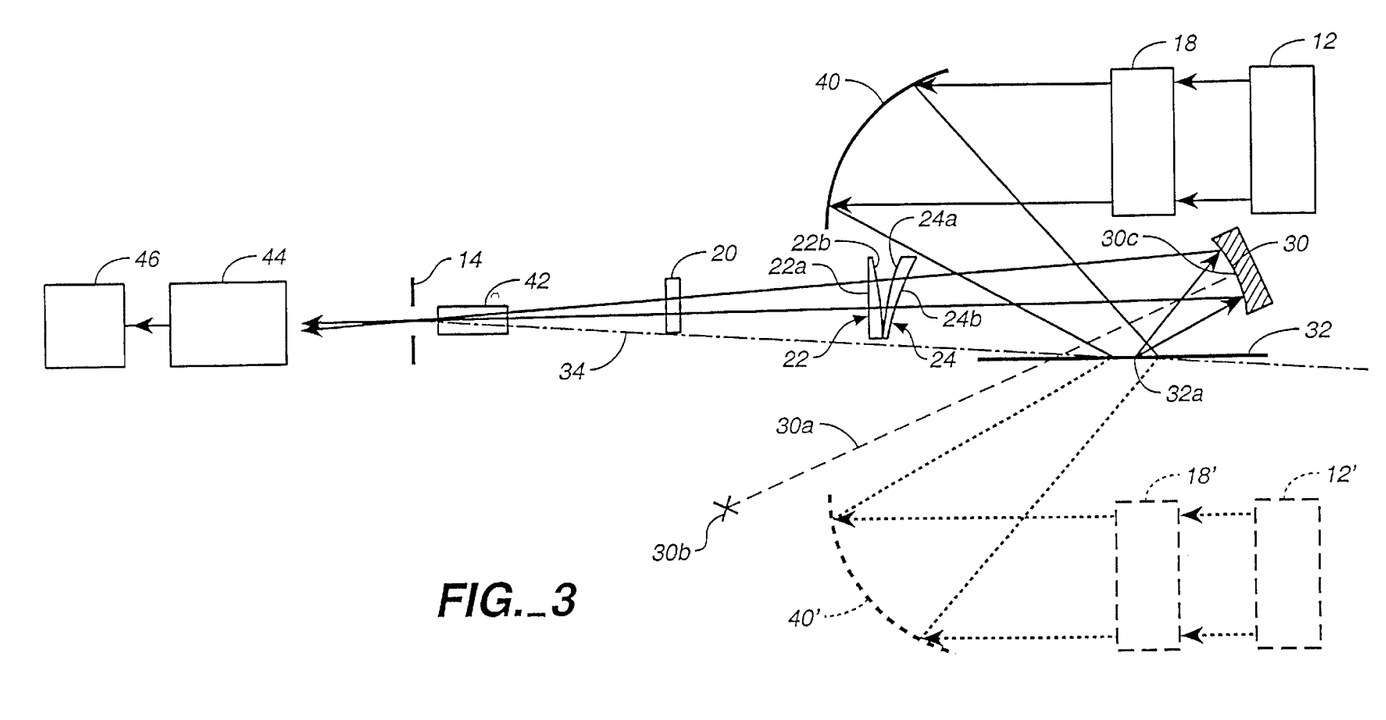
FIG. 3 is a schematic view of an ellipsometer where a spherical mirror and associated refractive elements are used for collecting radiation that has interacted with the sample to illustrate a third embodiment of the invention.

Instead of employing the optics comprising the mirror 30 and lenses 22, 24 in the illumination optics, it is also possible to employ such optics in the collection side as shown in FIG. 3. FIG. 3 is a schematic view of an ellipsometer 100 where a spherical mirror and associated refractive elements are used for collecting radiation that has interacted with the sample to illustrate a third embodiment of the invention. As shown in FIG. 3, radiation from source 12 is passed through polarizer 18 and focused onto the sample 32 by means of mirror 40. The radiation reflected from a small spot 32a of the sample is collected and focused by spherical mirror 30 through lenses 24, 22 and apodizer 20, analyzer 42 to aperture 14, and then to spectrometer 44. The output of the spectrometer 44 is supplied to computer 46 to determine the change in amplitude and phase of polarization caused by interaction of the sampling beam with the sample. Thus, the object is the spot 32a and the image is formed at the aperture 14, so that the dotted line 34 connecting them is the axis of the system 100. The size of the spot 32a is limited by aperture 14. Instead of detecting radiation that is reflected from the sample, it is again possible to detect radiation that is transmitted through (or otherwise modified by) the sample by source 12', after passing through polarizer 18' and focused by mirror 40', as shown in dotted lines in FIG. 3.

In the different embodiments of this invention, the apodizer 42 limits the numerical aperture of the sampling beam before reaching the mirror 30 in FIGS. 1 and 2 and that of the modified beam in FIG. 3 after reflection by the mirror 30 to preferably not more than 0.03. The angle of incidence of the sampling beam in FIGS. 1 and 2 and of the modified beam in FIG. 3 on the spherical mirror 30 preferably is within the range of 1 to 10 degrees from the axis 30a of the mirror. The Abbe numbers of lenses 22, 24 preferably do not differ by more than 2%.

The substantially achromatic optics comprising off axis spherical mirror 30 and elements 22, 24 may also be used for spectroscopic measurements other than ellipsometry, such as in scatterometry for measuring the line widths or other parameters of diffracting structures. When so used, it is possible to modify the configurations as shown in FIGS. 1–3 by omitting the polarizers and analyzers, or orient them to pass radiation with the same polarization states. Thus, in a more general application of the invention, the system of this invention provides a sampling beam of broadband radiation for interaction with a sample. An optics of the system focuses the sampling beam to a small spot on the sample, or radiation of the sampling beam that has interacted with the sample from a small spot of the sample into a modified beam. The optics includes a spherical mirror and at least two lenses. The sampling or modified beam is incident on the mirror from a direction away from an axis of the mirror, wherein at least one of the lenses corrects spherical aberration caused by off-axis reflection from the mirror. The system further comprises detection of radiation of the sampling beam that has interacted with the sample. In one preferred embodiment, the optics is substantially achromatic over visible and ultraviolet wavelengths. In another embodiment, at least one of the lenses in the optics is a meniscus lens that corrects spherical aberration caused by the off axis reflection by the spherical mirror. In yet another embodiment, the two lenses have substantially opposite magnification powers, so that the optics is substantially achromatic over a broadband of wavelengths.

While the invention has been described above by reference to various embodiments, it will be understood that different changes and modifications may be made without departing from the scope of the invention which is to be defined only by the appended claims and their equivalents.

What is claimed is:

1. An ellipsometer for performing spectroscopic scatterometric measurements on a sample having diffracting structures thereon, comprising:

a source which emits broadband radiation;

optics including a curved mirror, said optics focusing broadband radiation from the source in a sampling beam to a spot on the diffracting structures of the sample;

a polarizer that polarizes broadband radiation that is from the source and that is focused by the optics to the spot on the sample;

an analyzer that analyses radiation from the sampling beam that has interacted with the sample, thereby producing an output beam, wherein radiation reaching the analyzer from the source travels along an optical path;

a detector detecting the output beam to provide an output; and a processor processing the detector output to determine changes of polarization state in amplitude and phase of the sampling beam caused by interaction with the sample in order to measure parameters of the diffracting structure.

2. The ellipsometer of claim 1, further comprising at least one refractive element that compensates for aberration caused by the mirror.

3. The ellipsometer of claim 1, wherein said at least one refractive element is located in the optical path between the minor and the sample.

4. The ellipsometer of claim 1, wherein said optics focuses the sampling beam at an incidence angle of between about 60 degrees to about 80 degrees from a normal direction to the sample.

5. The ellipsometer of claim 1, further comprising an aperture placed in the optical path between the source and the polarizer, or between the polarizer and the optics.

6. The ellipsometer of claim 1, wherein said detector includes a spectrometer.

7. The ellipsometer of claim 1, wherein angle of incidence of the sampling beam to the axis of the mirror is substantially within the range of 1 to 10 degrees.

8. The ellipsometer of claim 1, said radiation comprising components having wavelengths in a range of at least about 250 to 800 nanometers.

9. The ellipsometer of claim 1, said radiation comprising components having wavelengths in a range of about 190 to 850 nanometers.

10. The ellipsometer of claim 1, said parameters comprising a line width.

11. A method for performing spectroscopic ellipsometry scatterometric measurements on a sample having diffracting structures thereon, comprising:

providing broadband radiation from a source;

focusing broadband radiation from the source in a sampling beam to a spot on the sample by means of optics that includes a curved mirror;

polarizing broadband radiation that is from the source and that is focused by the optics to the spot on the sample;

analyzing radiation from the sampling beam that has interacted with the sample by means of an analyzer, thereby producing an output beam;

detecting the output beam to provide a detected output; and processing the detected output to determine changes of polarization state in amplitude and phase of the sampling beam caused by interaction with the sample in order to measure parameters of the diffracting structure.

12. The method of claim 11, further comprising correcting for aberration caused by the mirror by at least one refractive element.

13. The method of claim 11, wherein said focusing focuses the sampling beam at an incidence angle of between about 60 degrees to about 80 degrees from a normal direction to the sample.

14. The method of claim 11, wherein said detecting includes dispersing the output beam according to wavelengths of radiation in the output beam.

15. The method of claim 11, said radiation provided comprising components having wavelengths in a range of at least about 250 to 800 nanometers.

16. The method of claim 11, said radiation provided comprising components having wavelengths in a range of about 190 to 850 nanometers.

17. The method of claim 11, said parameters measured comprising a line width.

18. An ellipsometer for performing spectroscopic scatterometric measurements on a sample having diffracting structures thereon, comprising:

a source which emits broadband radiation;

optics including at least one refractive element, said optics focusing broadband radiation from the source in a sampling beam to a spot on the diffracting structures of the sample;

a polarizer that polarizes broadband radiation that is from the source and that is focused by the optics to the spot on the sample;

an analyzer that analyses radiation from the sampling beam that has interacted with the sample, thereby producing an output beam, wherein radiation reaching the analyzer from the source travels along an optical path;

a detector detecting the output beam to provide an output; and a processor processing the detector output to determine changes of polarization state in amplitude and phase of the sampling beam caused by interaction with the sample in order to measure parameters of the diffracting structure.

19. The ellipsometer of claim 18, optics further comprising a curved mirror, wherein said at least one refractive element is located in an optical path between the mirror and the sample.

20. The ellipsometer of claim 18, wherein said optics focuses the sampling beam at an incidence angle of between about 60 degrees to about 80 degrees from a normal direction to the sample.

21. The ellipsometer of claim 18, further comprising an aperture placed in an optical path between the source and the polarizer, or between the polarizer and the optics.

22. The ellipsometer of claim 18, wherein said detector includes a spectrometer.

23. The ellipsometer of claim 18, said curved mirror having an axis, wherein angle of incidence of the sampling beam to the axis of the mirror is substantially within the range of 1 to 10 degrees.

24. The ellipsometer of claim 18, said radiation comprising components having wavelengths in a range of at least about 250 to 800 nanometers.

25. The ellipsometer of claim 18, said radiation comprising components having wavelengths in a range of about 190 to 850 nanometers.

26. The ellipsometer of claim 18, said parameters comprising a line width.

27. A method for performing spectroscopic ellipsometry scatterometric measurements on a sample having diffracting structures thereon, comprising:

providing broadband radiation from a source;

focusing broadband radiation from the source in a sampling beam to a spot on the sample by means of optics that includes at least one refractive element;

polarizing broadband radiation that is from the source and that is focused by the optics to the spot on the sample;

analyzing radiation from the sampling beam that has interacted with the sample by means of an analyzer, thereby producing an output beam;

detecting the output beam to provide a detected output; and processing the detected output to determine changes of polarization state in amplitude and phase of the sampling beam caused by interaction with the sample in order to measure parameters of the diffracting structure.

28. The method of claim 27, wherein said focusing focuses the sampling beam at an incidence angle of between about 60 degrees to about 80 degrees from a normal direction to the sample.

29. The method of claim 27, wherein said detecting includes dispersing the output beam according to wavelengths of radiation in the output beam.

30. The method of claim 27, said radiation provided comprising components having wavelengths in a range of at least about 250 to 800 nanometers.

31. The method of claim 27, said radiation provided comprising components having wavelengths in a range of about 190 to 850 nanometers.

32. The method of claim 27, said parameters measured comprising a line width.

* * * * *